United States Patent
Theron et al.

(10) Patent No.: US 9,618,427 B2
(45) Date of Patent: *Apr. 11, 2017

(54) SAMPLING SEPARATION MODULE FOR SUBSEA OR SURFACE APPLICATION

(71) Applicant: Schlumberger Technology Corporation, Sugar land, TX (US)

(72) Inventors: Bernard E. Theron, Aberdeen (GB); Malcolm Atkinson, Aberdeen (GB); Andrea Sbordone, Costa del Sol (SG); John Allan Nighswander, Houston, TX (US); Rune Lien, Kongsberg (NO)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 161 days.

This patent is subject to a terminal disclaimer.

(21) Appl. No.: 14/381,988

(22) PCT Filed: Mar. 1, 2013

(86) PCT No.: PCT/US2013/028496
§ 371 (c)(1),
(2) Date: Aug. 28, 2014

(87) PCT Pub. No.: WO2013/130924
PCT Pub. Date: Sep. 6, 2013

(65) Prior Publication Data
US 2015/0007648 A1    Jan. 8, 2015

Related U.S. Application Data

(60) Provisional application No. 61/605,860, filed on Mar. 2, 2012.

(51) Int. Cl.
*G01N 1/10* (2006.01)
*E21B 49/08* (2006.01)
(Continued)

(52) U.S. Cl.
CPC ............... *G01N 1/10* (2013.01); *E21B 49/08* (2013.01); *G01N 1/2035* (2013.01); *G01N 33/28* (2013.01);
(Continued)

(58) Field of Classification Search
CPC ......... E21B 49/08; E21B 49/001; G01N 1/10; G01N 1/2202; G01N 1/2035; G01N 1/02;
(Continued)

(56) References Cited

U.S. PATENT DOCUMENTS 5,134,879 A    8/1992   Wong et al.
5,473,939 A  * 12/1995  Leder ..................... E21B 23/06
                                                        166/264

(Continued)

FOREIGN PATENT DOCUMENTS

EP        164863        12/1985
EP       1645863 B1      4/2006
(Continued)

OTHER PUBLICATIONS

International Search Report and Written Opinion issued in the related PCT application PCT/US2013/028496, dated Jun. 24, 2013 (9 pages).

(Continued)

*Primary Examiner* — Blake A Tankersley
(74) *Attorney, Agent, or Firm* — Rodney Warfford; Matt Jorge

(57) ABSTRACT

The disclosure describes a system to segregate, enrich and capture oil, water and gas samples from a multiphase flow. The system can be used in a subsea location, on the surface or in any other condition where it is connected to a flow of different phases of gas and/or liquid. The samples obtained are representative in composition of the phases flowing at well head conditions in terms of both pressure and tempera- (Continued)

ture. Additionally, a relatively small volume of each phase is used in obtaining the samples. The system connects and disconnects to ports installed at the sampling location nearby the wellhead or the production line. The sampling flow is controlled by means of a pump. The collected samples are separated in mono (or nearly mono)—phase samples (oil, water and gas) and stored in individual bottles.

22 Claims, 3 Drawing Sheets

(51) Int. Cl.
    *G01N 33/28*      (2006.01)
    *G01N 1/20*      (2006.01)

(52) U.S. Cl.
    CPC . *G01N 33/2823* (2013.01); *G01N 2001/1031* (2013.01)

(58) Field of Classification Search
    CPC ... G01N 2001/1062; G01N 2001/1031; G01N 33/2823; G01N 33/28; B01D 17/02; B01D 19/00; B01D 19/0073
    See application file for complete search history.

(56) References Cited

U.S. PATENT DOCUMENTS

| | | | |
|---|---|---|---|
| 6,182,505 B1 * | 2/2001 | Segeral | G01N 1/2035 422/68.1 |
| 6,435,279 B1 | 8/2002 | Howe et al. | |
| 9,068,436 B2 * | 6/2015 | Theron | E21B 27/00 |
| 2007/0143023 A1 | 6/2007 | Betancourt et al. | |
| 2008/0016944 A1 * | 1/2008 | Legrand | G01N 33/2823 73/25.01 |
| 2010/0059221 A1 | 3/2010 | Vannuffelen et al. | |
| 2010/0313849 A1 * | 12/2010 | Stoner | F02D 41/22 123/350 |
| 2011/0005765 A1 | 1/2011 | Cumming et al. | |
| 2011/0040501 A1 * | 2/2011 | Martin | E21B 47/10 702/45 |
| 2011/0061475 A1 * | 3/2011 | Guieze | G01N 1/2035 73/864 |
| 2012/0267115 A1 * | 10/2012 | Brown | E21B 41/0007 166/336 |
| 2013/0025854 A1 | 1/2013 | Theron et al. | |

FOREIGN PATENT DOCUMENTS

| | | | | |
|---|---|---|---|---|
| GB | 2445745 A | | 7/2008 | |
| GB | 2460668 B | | 8/2012 | |
| WO | WO-2006037565 | * | 4/2006 | ............... G01N 1/20 |
| WO | 2008/087156 | | 7/2008 | |
| WO | 2010/106499 | | 9/2010 | |
| WO | 2010/106500 | | 9/2010 | |

OTHER PUBLICATIONS

International Preliminary Report on Patentability issued in the related PCT application PCT/US2013/028496, dated Sep. 2, 2014.

* cited by examiner

SAMPLING SEPARATION MODULE FOR SUBSEA OR SURFACE APPLICATION

CROSS REFERENCE TO RELATED APPLICATIONS

This patent application claims the benefit of U.S. Prov. Ser. No. 61/605860 filed on Mar. 2, 2012, which is incorporated by reference herein.

BACKGROUND

Fluid being produced from a wellbore or flowing through production lines is often multiphase—commingled flow of different phase fluids, such as water, oil and gas. Multiphase fluid flow is a complex factor, important in understanding and optimizing production hydraulics in both oil and gas wells. Sampling some or all of the individual phases from a multiphase flow presents particular problems, such as separation and accumulation of the desired phase. Additionally, there can exist a relatively large range of flowing conditions such as high to low Gas Volume Fraction (GVF) and high to low Water Liquid Ration (WLR). Furthermore, a large variety of sampling ports configurations may be present. The challenges can be even greater in the context of sub-sea multiphase sampling.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a system for separating and sampling fluid from a multiphase fluid is described. The system includes: a separation chamber; an inlet port operatively connected to the separation chamber; an upper outlet port operatively connected to the separation chamber at a location above the inlet location; a lower outlet port operatively connected to the separation chamber at a location below the inlet location; and a pumping system adapted and configured to circulate fluid into the separation chamber via the inlet port and out of the separation chamber via the upper outlet port or the lower outlet port, wherein a desired fluid phase is accumulated within the separation chamber. According to some embodiments, sensors are configured and operatively connected to make measurements indicative of phase content of fluid passing through the upper and lower outlet ports. Examples of phases in the multiphase fluid include gas, oil, and water, although other types of fluid phases can be separated and sampled.

According to some embodiments, a number of valves are operatively connected so as to control flow at the upper and lower outlet ports. The pumping system can include reciprocating pistons within two cylinders that are tilted from a horizontal plane such that a degree of pre-separation of the phase can occur within the cylinders. The separation system can include a housing adapted and configured to house the separation chamber and pumping system, and to be deployed in a subsea setting using for example a remotely operated underwater vehicle (ROV) or autonomous underwater vehicle (AUV).

According to some embodiments, a method for separating and sampling fluid from a multiphase fluid flow is described. The method includes: drawing a multiphase fluid from the multiphase fluid flow at a first multiphase fluid port; pumping the multiphase fluid through an inlet port into a separation chamber at an inlet location; allowing fluid to exit the separation chamber at either (1) an upper outlet port operatively connected to the separation chamber at a location above the inlet, or (2) a lower outlet port operatively connected to the separation chamber at a location below the inlet; and returning fluid having exited the separation chamber to the multiphase fluid flow at a second multiphase fluid port, wherein a desired fluid phase is accumulated within the separation chamber through a circulation of the fluid through the separation chamber. According to some embodiments, the multiphase fluid includes a gas phase, an oil phase and a water phase. When the desired fluid phase is the gas phase, the fluid is allowed to exit the separation chamber at the lower outlet port until the onset of the gas phase exiting the lower port is sensed, indicating the separation chamber is at least nearly full of the gas phase, and flowing the accumulated gas phase from the separation chamber by closing the lower port, opening the upper port and directing the gas to a sample bottle while continuing the pumping until sample bottle is full or liquid is sensed at upper port. When the desired fluid phase is the water phase or the oil phase, the fluid is allowed to exit the separation chamber at the upper outlet port until the onset of the water phase exiting the upper port is sensed, indicating the separation chamber is at least nearly full of the water phase, and flowing the accumulated water phase from the separation chamber by opening the lower port, closing the upper port and directing the water to a sample bottle while continuing the pumping until sample bottle is full or gas is sensed at lower port. When the oil phase is the desired phase, an alternating sequence is carried out of (1) allowing fluid to exit the upper port until the onset of a liquid phase exiting the upper port is sensed and (2) allowing fluid to exit the separation chamber at the lower outlet port instead of the upper port until onset of the oil phase exiting the lower outlet port is sensed. The alternating sequence is carried out until an adequate volume of the oil phase has been accumulated in the separation chamber. According to some embodiments, the gas, water and oil are accumulated in a sequence so as to decrease a total accumulation time.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein.

DETAILED DESCRIPTION

Figure 1:
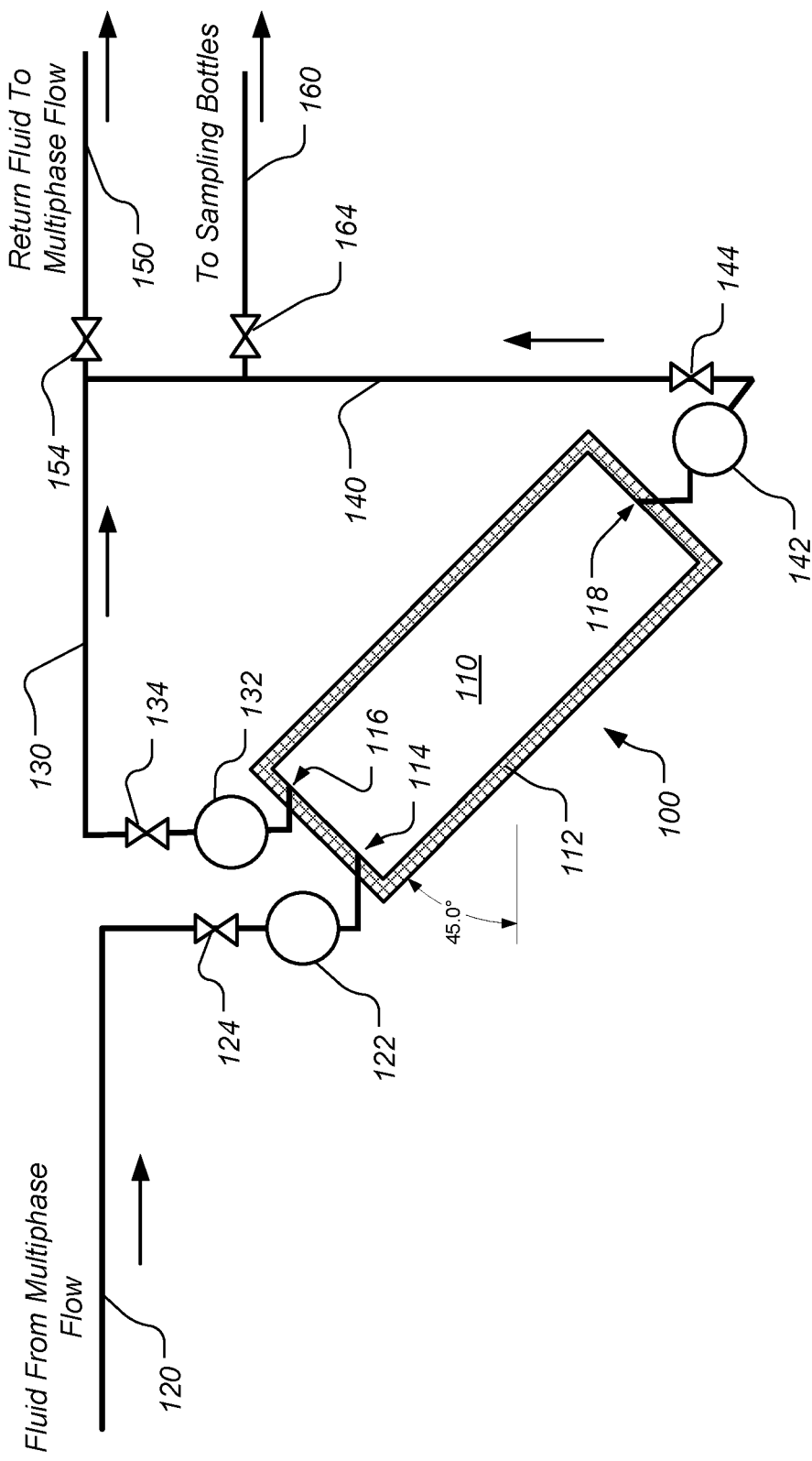
FIG. 1 is a diagram showing aspect of a chamber for separation of multiphase fluids, according to some embodiments.

The particulars shown herein are by way of example, and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details of the subject disclosure in more detail than is necessary for the fundamental understanding of the subject disclosure, the description taken with the drawings making apparent to those skilled in the art how the several forms of the subject disclosure may be embodied in practice. Further, like reference numbers and designations in the various drawings indicate like elements.

According to some embodiments, a robust method for providing oil, water and gas samples from a production flow in subsea or surface environment for a large range of flowing conditions (high to low Gas Volume Fraction (GVF) and Water Liquid Ration (WLR)) and fluid properties, is described. The method uses an inlet and outlet sampling port and is also able to cope with a large variety of sampling ports configurations. For example, sampling with ports at same pressure and ports with a large pressure difference can be accommodated.

According to some embodiments, the first stage, connecting and getting fluids from the line can be made in several ways depending on the specific configuration of the installation. Due to a lack of common standards applied by the wellhead manifold manufacturers, the sampling system, according to some embodiments is able to cope with various types of ports.

In order to capture a certain volume of each phase in a wide range of flow conditions, for example at very high WLR or at very low WLR, the system separates each phase and accumulates the quantity of the required phase, through a process commonly known as phase enrichment. The enrichment process is made at the same temperature and pressure as the flowing line to avoid phase composition changes and to ensure that the sample is representative of the phases in the conditions of the multiphase flow from which the sample is being extracted.

According to some embodiments, the enrichment process is continuous and the un-wanted fluids are discharged to the multiphase flow. A flexible and adaptable method of sampling flow generation/regulation across the enrichment system is described herein. In case of subsea operations, the samples can be stored in sampling bottles taken back to surface where further enrichment can be made if desired. According to some embodiments, the sample bottles are be analysed in a subsea location upon separation. In case of surface operations, the samples are directly collected in the sampling bottles and sent for analysis. There are several related references including U.S. Pat. No. 6,435,279, US2011/0005765, EP164 863, GB2445745, GB2460668, WO2010/106499, and WO2010/106500, each of which is incorporated by reference herein.

According to some embodiments, the described systems and techniques are designed for optimal function through the use of sensors. Due to a fault-tolerant architecture, the sampling system can still perform its functionalities even in case of failure of one or more of the sensors. The sampling process allows the sampling sequences of the three phases to overlap in time therefore reducing the total sampling duration for the three phases.

According to some embodiments, the technique includes a system and method to capture samples of oil, water and gas or other phases which can separate by gravity, enrich the quantity of the desired phase and then dispose the unwanted phases and direct the desired phase to a sample container or bottle.

FIG. 1 is a diagram showing aspect of a chamber for separation of multiphase fluids, according to some embodiments. The separator container 100 includes a separation space 110 that is bounded by container wall 112. The container 100 has at least three ports—two in the upper area of the container (ports 114 and 116) and one in the lower area of the container (port 118). According to some embodiments, at least one of the ports is equipped (at or near the port) with a sensor, which detects one or more properties of the flow passing through the port. For example, the sensor can be an optical phase detector, or a resistivity probe. In the example shown in FIG. 1, each of the ports 114, 116 and 118 have sensors to measure properties of the fluid flowing therethrough, namely sensors 122, 132 and 142 respectively. According to some embodiments, the separation container can have different orientations, going from a few degrees of inclination from the horizontal position, all the way to be completely vertical. In the case of the embodiment shown in FIG. 1, the container 100 is inclined 45 degrees from horizontal.

In the example shown in FIG. 1, port 114 is the inlet port through which the multi phase flow enters the container 100. When valve 124 is opened, the multi phase liquid flows through fluid line 120, for example via actuation of a pumping system, through sensor 122 and then through port 114. Ports 116 and 118 are outlet ports of the container 100. Through the activation of valve 134 on line 130, valve 144 on line 140, valve 154 on line 150 and valve 164 on line 160, ports 116 and 118 are outlet ports, each of the ports 116 and 118 can be selectively connected to either to line 150 for returning fluid to the multiphase flow, or line 160 for feeding fluid into one or more sample bottles for sample storage. By operating the system described above in different sequences, it is possible to perform the phase separation, enrichment and selection required to capture a sufficient volume of each phase from a multiphase flow, as further described below.

According to some embodiments, a system is described that creates and controls a sampling flow rate across an enrichment system between two ports located on a multiphase flow line, and allows the safe and early detection of well fluid leaks.

According to some embodiments, the ports are located such that each phase can be sampled from at least one of them. In an ideal case, gas is collected from one port only, while a liquid mixture is collected from the other port only. However, the disclosed system can also operate sufficiently in cases where there is a predominant gas port or a predominant liquid port. In practice, it has been found that there is typically at least one predominant phase port. In the case of high GVF (Gas Volume Fraction) wells the gas port will be an exclusive gas port while the liquid port will get some portion of gas in it. Conversely, in low GVF wells the gas port may get some liquid, but the liquid port will be exclusively liquid. According to some embodiments, the principles of the system described herein will nevertheless apply to the case of two generic ports connected to a multiphase flow.

Figure 2:
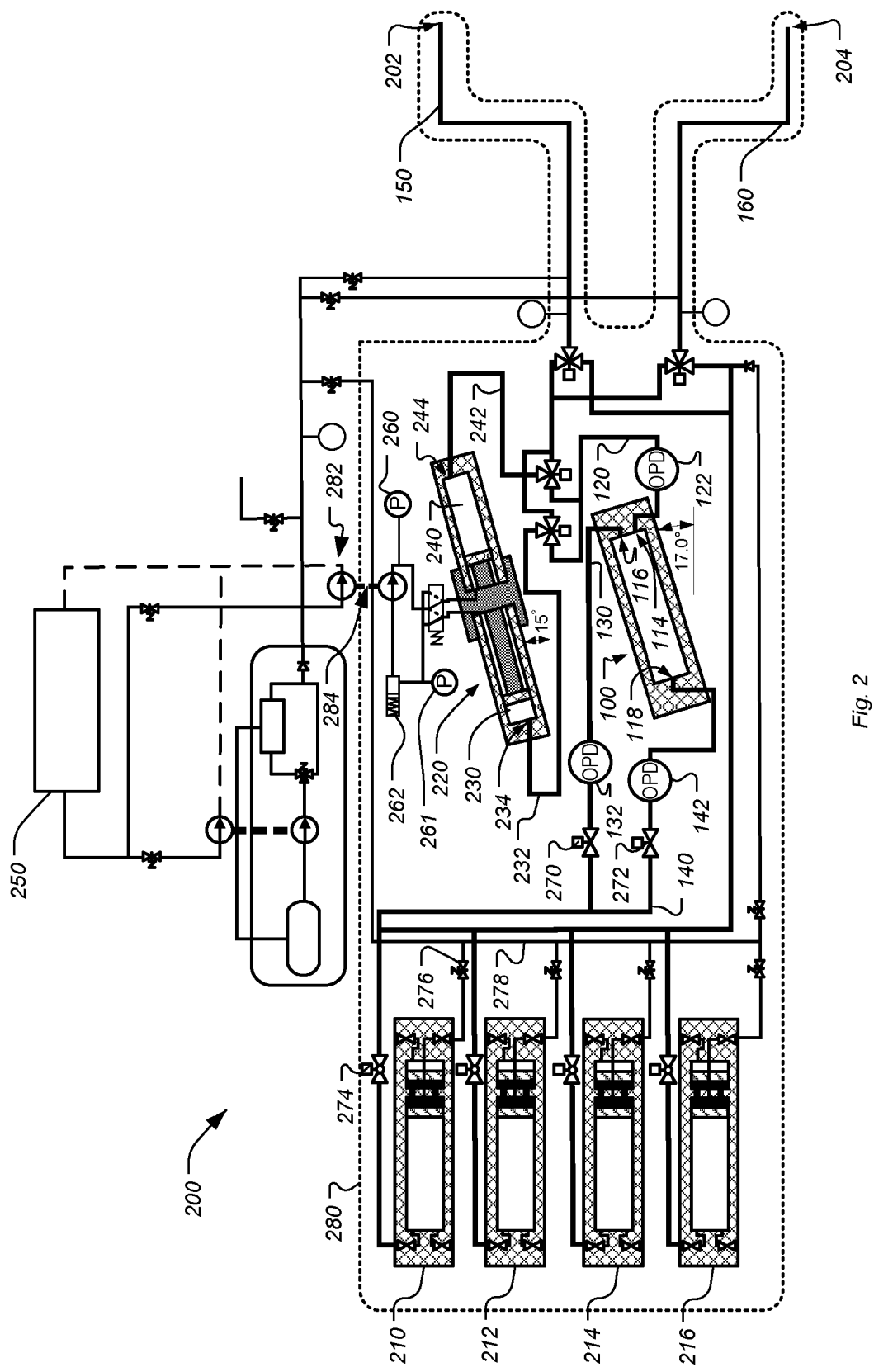
FIG. 2 is a diagram showing aspects of a system for separating and sampling fluid from a multiphase fluid.

FIG. 2 is a diagram showing aspects of a system for separating and sampling fluid from a multiphase fluid. In the example shown in FIG. 2, the creation and control of the sampling flow rate across the enrichment system is accomplished by using a multiphase pump 220 made of a reciprocating dual cylinder. This type of pump allows for some amount of pre-separation, which has been found to significantly decrease the full process time. Additionally, according to some embodiments the pump is able to detect leaking of well fluid from the pump cylinders 230 and 240. The location of the pump ports 234 on cylinder 230 and 244 on cylinder 240, and the orientation of the pump are selected to favor the pre-separation and minimize the re-mixing of the fluid within the pump. In the example shown in FIG. 2, the pump 220 is oriented about 15 degrees from horizontal, although other orientation angles can be used depending on the application. A pressure sensor is mounted on the hydraulic tank side to detect eventual leaks of the well fluid from the pump cylinders 230 and/or 240. The configuration of the pistons within the pump 220 is such that the pressure in the hydraulic tank side is close to the environmental pressure. Any leakage of well fluid larger than the capacity of the compensation system 262 will trigger an increase in pressure, revealing a leak. The capacity of the pressure compensation system 262 ensures that the normal small fluid exchange at the dynamic seals of the pistons will be absorbed without triggering a false alarm. A more important leak would be contained in the hydraulic circuit and detected before spreading any further. According to some embodiments, hydraulic circuit contamination could also be determined using a phase detector similar to the ones used for the sampling as described below.

The system shown in FIG. 2 enables the concentration of any desired phase (gas, oil or water) such that sufficient volume of the desired phase can be collected under a wide range of flow line conditions (e.g. large range of GVF, water cut and/or total flow rate). The concentration of each desired phase is addressed by using a small separation container 100, which according to some embodiments is an existing sampling bottle or according to other embodiments, is a purpose built container. The container 100 is equipped with two ports on the upper end, one inlet 114 and one top outlet 116, and one at the lower end, outlet 118. On each port line a phase detector may be installed (122, 132, 142). According to some embodiments the detectors 122, 132 and 142 are optical phase detectors, although according to other embodiments, the phase detectors are of other types. The function of detectors 122, 132 and 142 is to identify which phase is flowing across the port. The container 100 may be installed on a tilted position to favor the separation. In FIG. 2, the container 100 is tilted about 17 degrees from horizontal, although according to some embodiments the container is tilted other amounts depending on the anticipated application. The 3-phase mixture fluid coming from the pump 220 enters the separation container 100 through the inlet port 114 at a controlled speed set by the pump rate. Depending upon which phase is desired, either the top exit port 116 or bottom exit port 118 is opened while the pump is running ensuring a moderate three phase flow and enough residence time of the mixture in the separation container 100.

To accumulate gas, the well fluid is circulated from the gas-rich sample port 202 and unwanted fluid is returned to the liquid-rich port 204. The top outlet valve 270 of the separator is closed while the bottom outlet valve 272 is open. Therefore the gas is trapped and accumulates in the top of the container 100 while the liquid runs quickly out at the bottom and is naturally expelled. The bottom phase detector 142 determines when gas starts to come out of port 118, which reveals that the separation container 100 is nearly full of gas and is therefore ready to be transferred to one of the storage bottles 210, 212, 214 or 216. This operation can be made manually by the operator monitoring the bottom phase detector signal and need not rely on precise timing. The operator only waits long enough to make sure gas is detected at the bottom detector 142. Waiting a longer time will simply allow the pumped gas to exit the separation container 100, but the container 100 will remain full of gas. According to some embodiments, the controls are automated to reduce or eliminate monitoring by a human. The position of the inlet port 114 and top outlet port 116 in the separation chamber makes it possible for the three phase mixture entering the separator to split between liquid and gas, with gas flowing out by the top outlet port 116 and liquid accumulating at the bottom of container 100. In order to transfer the accumulated gas phase to the sampling bottle, the bottom port valve 272 is closed and the top port valve 270 is opened and the flow from the container 100 is directed to one or more of the gas sampling bottles 210, 212, 214 and 216 each of which is equipped with a piston. In the example transferring fluid to the sampling bottle 210, bottle inlet valve 274 is open to the separator line while the buffer line valve 276 (located other side of the internal piston) is opened to the outlet sampling line. In this way, the pressure in the bottle 210 is maintained at or near the pressure of the multiphase flow, and the pump 220 only has to overcome the pressure losses in the circuit and the friction of the piston seals in the sampling bottle. The volume of gas transferred to the bottle is estimated from the volumetric pump (1). According to some embodiments, the separator volume is preferably equal to or greater than at least the volume of one of the sampling bottles 210, 212, 214 and 216, such that a single gas accumulation sequence will be enough to fill up a sample bottle. For increased time efficiency, the liquid accumulated in the separation chamber during the gas transfer will be ready for the next liquid sampling sequence. According to some embodiments, the gas accumulation phase can be part of an initial cleaning sequence made to remove the flushing liquid from the system after pressure testing the system connections. This flushing sequence is made in the same way as the gas accumulation phase; it consists of removing the liquid by pushing it out of the separator with gas. Therefore, at the end of the flushing phase, the gas is already accumulated and ready to transfer, shortening the full process duration.

The water is accumulated in the separation container 100 by opening the top outlet valve 270 and closing the bottom outlet valve 272 while the pump 220 is providing the three-phase mixture. The water separates from the oil/gas and accumulates at the bottom of the separation chamber 100. Utilizing the previous gas sampling sequence enables the technique to take advantage of the amount of liquid already accumulated and therefore shorten the sequence duration. The detection of the water at the top of the separator by the phase detector 132 indicates the container 100 is full of water. The detection of this point may in some cases be ambiguous, notably when little water is present in the three-phase flow stream. However, during the following transfer phase the operator will be in a good position to measure the amount of water actually accumulated in the container 100 and can then estimate the duration of an additional water collection sequence if desired. To transfer the water to the storage bottle, the top outlet port valve 270 is closed and the bottom port valve 272 is opened and the flow from the container 100 is therefore directed to one of the sampling bottles 210, 212, 214 or 216 while the pump 220 is still running The sampling bottle buffer line 278 is connected to the outlet sampling line to maintain the sample pressure at the same pressure of the multiphase flow. The bottom phase detector 142 is monitored to detect oil or gas getting to the bottom exit port, in this case the detection is easy as the detector 142 is fully immersed in water and as soon as the water is emptied from container 100 some oil or gas will begin to flow trough and detected by detector 142. At this point, or if the desired volume is reached first, the transfer is stopped. The transferred volume can be estimated from the volumetric pump 220. After the first transfer is made, the water capture efficiency can be evaluated from the total amount of sample pumped in and the volume of water captured during the sequence. This evaluation can then be used to estimate the additional time, if desired, in order to accumulate the desired amount of water, according to some embodiments.

Accumulating the oil requires purging the water at the bottom of oil in container 100. If this sequence is started immediately following a previous water sampling sequence, the separation container already contains some oil at the bottom with gas on the top. The bottom outlet valve 272 is closed and top outlet valve 270 is opened while the pump 220 is running The liquid begins to accumulate with water at the very bottom of container 100, oil on top of the water, and gas at the top of the container 100. As soon as liquid is detected on the top outlet detector 132, the top outlet valve 270 is closed and bottom outlet valve 272 is opened. The water is then pumped out and discharged to the outlet port (either port 202 or port 204) until oil is detected at the bottom sensor 142. The cycle is then repeated, closing the bottom outlet valve 270, opening the top outlet valve 272, to accumulate more oil until liquid is again detected coming out at top outlet detector 132. The process is repeated, with each iteration becoming shorter and shorter as more oil is accumulated (enriched) in the separation container 100. When an adequate volume of oil is accumulated, the oil can be transferred to one of the sampling bottles. The transfer can be operated in two ways, from the bottom or from the top of the separator, depending which sampling ports 202 or 204 is the most monophasic. If the well conditions are high GVF, the gas-rich port 202 is likely the most suitable as nearly no liquid is caught from it, while a low GVF well will make the liquid-rich port 204 exclusively liquid (or nearly so). The observation of the inlet detector 122 during the previous sampling sequences can be used to indicate which of the sampling ports 202 or 204 is the most adequate to use as an inlet/outlet during the transfer of oil from container 100. If the gas-rich port 202 is the best in providing a monophasic flow, consisting of gas in this case, the inlet sample stream is connected to this gas-rich port, the bottom outlet valve 272 is opened and top outlet valve 270 is closed. Any water is discharged to the multiphase flow (via port 204), and then by operating the various valves the oil is directed to an oil storage bottle for transfer. The gas stream that fills up the separation container 100 pushes out the oil at the bottom port 118 until the required volume of oil is transferred or gas is detected at the bottom sensor 142. In this latter case, a new oil collection sequence can be repeated. According to some embodiments, the separation chamber volume is selected to be greater than then the desired sample volume. In such cases repeat sequences can be avoided.

Conversely if the liquid port 204 is better in providing a monophasic flow, liquid rich in this case, the bottom outlet port valve 272 is closed, top port valve 270 is opened and the flow coming out of the upper port 116 is directed to the sampling bottles. The additional oil coming into the separation container 100 and the water accumulating at the bottom of the container act to expel the oil into to the storage bottle.

During the previously described collecting sequences the separation of the phases is made in the separation container. According to some embodiments, the pump 220 is used to provide a degree of pre-separation of the phases. This pre-separation in the pump 220 has been found to be particularly useful when: (1) the phases do not separate well, in which case the pump 220 will contribute to the separation performed in the separation container 100 itself, therefore making the system more efficient; and (2) a relatively small amount of one phase is present in the sample stream. In this latter case it is easier to detect the low concentration phase with the detectors (especially inlet detector 122) if the phase is concentrated in small slugs rather than dispersed throughout the sample stream.

According to some embodiments, the ability to detect when the separation between the phases is slower than expected, particularly between oil and water, is provided. This allows the user to pause the sampling flow and to allow more separation time once the separator is full of liquid mixture.

This is accomplished by using the local optical phase detectors 122, 132 and 142, located in the flow stream itself. According to some embodiments, other types of detectors able to discriminate oil, water and gas can be used for the same purpose. For example, an infrared type detector, a resistivity detector, or a combination of different types of detectors can be used. The nature of the signal may be indicative of the size of the oil/water/gas bubbles. If the size of the bubble becomes smaller than the sensor tip (e.g. <100 microns) the signal departs from its typical binary behavior. Comparing the signal of the inlet probe detector 122 to the outlet probe detectors 132 and 142 provides a way to estimate if the separation in the separator is effective and reacts effectively to the sampling rate. Thus, according to some embodiments, the signals from the detectors can be used to give an indication of the effectiveness of the separation and if the separation is not effective the pumping rate (i.e. the sampling rate) can be adjusted to improve the effectiveness of the separation by varying the effective retention time in the separation chamber.

According to some other embodiments, the ability to check/evaluate the sample volume that has been captured is provided. The sampling rate is controlled by using a volumetric pump 220; by counting the stroke by means of a proximity detector on the piston and counting the revolutions used to drive hydraulic pump 220. The stroke signal provides an accurate volume at one stroke resolution, while the revolution counts on the hydraulic pump allow increasing the volume resolution on each stroke. An automatic adjustment of the revolution per stroke may be calculated at each stroke end to take into account the inherent random drifts of the hydraulic pump 220.

According to some other embodiments, the ability to work in degraded mode if the phase detectors fail or are fouled, is provided. The operating mode of the system can be downgraded to backup modes in case of phase detector failure. According to some embodiments, the system can operate without using any of the phase detectors 122, 132 and 142 when sampling gas and water, and the system can operate with only the phase detector 132 on the upper outlet port 116 when sampling oil. To accumulate water in the separation container 100 without use of the phase detectors, fluid flow is introduced to the separation container 100 while the upper exit port 116 is open for a suitably long period (e.g. determined from previous sampling operation at the site). The system will then accumulate water in the bottom of the separation container 100. Similarly, pumping with the bottom exit valve 272 open for a suitably long period will accumulate gas in the separation container 100. In order to accumulate oil, according to some embodiments, the upper outlet detector 132 is used at least to detect between liquid and gas. With such an indication it is possible to accumulate liquid with top exit valve 270 open until liquid is detected at detector 132. At this point the bottom port 118 is opened and half of the volume of the separation container 100 is pumped in. This will expel the water at the bottom of container 100 but keep at least half of the top liquid where the oil will accumulate. After repeating this sequence several times the separator will be at least full with 50% of oil which can then be transferred to the storage bottle(s). The volume of oil transferred can be monitored by observing the signal from probe 132 during the transfer to the storage bottle. A new sequence can then be re-started if necessary to obtain more oil.

According to yet some other embodiments, samples are kept close to line pressure and temperature during the enrichment process to ensure a representative sample, and the samples are safely stored at a desired pressure and temperature for sample integrity. This can be ensured by insulating and/or actively heating the sampling system in the area outlined by dotted line 280. To avoid loss of heat with the hydraulic fluid the pump circuit may be located in the thermally controlled zone. To avoid heat loss at the pump, the pump may be located within the insulated zone, but powered with a motor 282 located outside the thermal zone and linked to the pump with an insulated shaft 284. According to some other embodiments, selected enriched sample is pushed into a sampling bottle by means of a rodded piston in the separator with a conduit passing through the rod, so that the piston can be pushed up into the separator, expelling the sample either from the top exit port or from the port connected to the conduit passing through the piston.

According to some embodiments, the flow within the separation system is generated by differential pressure between the inlet and outlet ports 202 and 204 instead of through the use of a pumping system. According to some embodiments, the separation system described herein is used to separate liquid phases other than oil and water. According to some embodiments, a plurality of sensors can be used to detect a level of each phase within the separation container. According to some other embodiments, the separation container includes a window such that an operator can visually monitor the phases present in the container. According to some embodiments, the visual monitoring is performed using a video camera or an indirect measurement light EMR transmittance. According to some embodiments, one or more chemicals are mixed with the flow to facilitate the separation of the phases.

Figure 3:
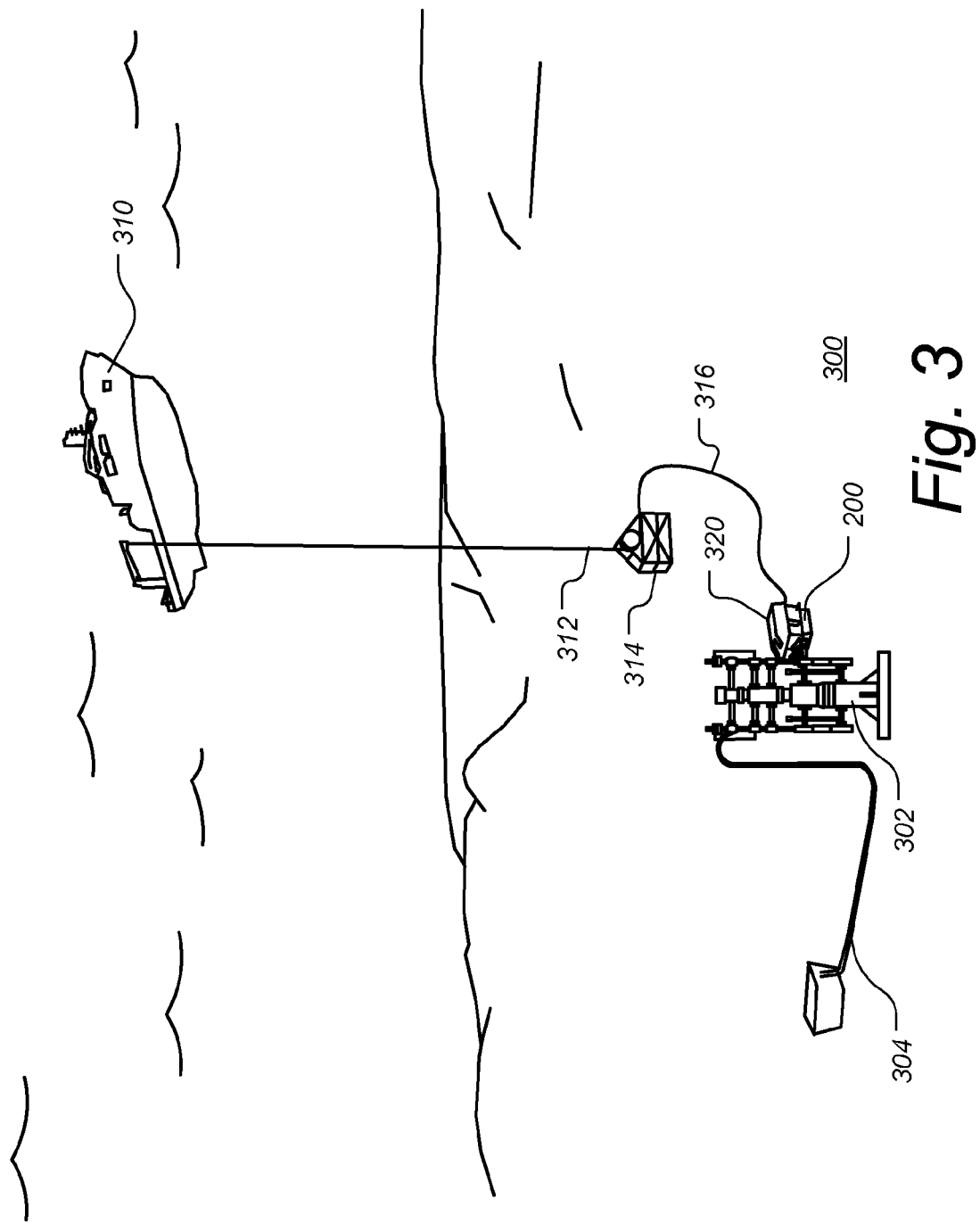
FIG. 3 is diagram illustrating a system for separating and sampling multiphase fluid deployed in a sub-sea setting, according to some embodiments.

FIG. 3 is a diagram illustrating a system for separating and sampling multiphase fluid deployed in a sub-sea setting, according to some embodiments. In the example of FIG. 3, the multiphase separation and sampling system 200, which is shown and described with respect to FIGS. 1 and 2, is deployed on a sea floor 300 via a remotely operated underwater vehicle (ROV) 320. ROV 320 is controlled and powered from the surface by an operator/pilot via an umbilical or using remote control. In the case shown in FIG. 3, the ROV operator is located in a surface vessel 310. The ROV is tethered using a main lift umbilical 312 to tether management system 314, which manages the free-swimming tether 316 to the ROV 320. The separator system 200 is attached to the ROV 320 for deployment, for example via the skids of ROV 320. The ROV 320 is also used to make the multiphase connection, i.e. the connections between the gas-rich port 202 (not shown) and liquid rich port 204 (not shown) of system 200 to the subsea tree 302 for a producing wellbore to one or more hydrocarbon-bearing subterranean reservoirs. Note that while the example shown in FIG. 3 shows the system 200 being connected to a subsea tree 302, according to other embodiments the separation and sampling system 200 is connected to multiphase flow lines at other locations. For example, according to some embodiments, the sampling system is attached to a sea floor pipeline 304 via ROV 320. In this case, the gas-rich port of system 200 can be connected near the top of the pipeline 304, while the liquid-rich port of system 200 can be connected near the bottom of the pipeline 304. According to some embodiments the system 200 is deployed using an autonomous underwater vehicle (AUV), without using input from an operator. Note that while the system 200 is shown being deployed in a subsea location in FIG. 3, according to some embodiments, the system 200 is deployed in surface locations such as to sample multiphase flow at surface wellsites or on surface flow lines.

While the subject disclosure is described through the above embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the subject disclosure should not be viewed as limited except by the scope and spirit of the appended claims.

What is claimed is:

1. A system for separating fluid from a multiphase fluid including gas, oil, and water, the system comprising:
 a separation chamber;
 an inlet port operatively connected to the separation chamber at an inlet location for flowing multiphase fluid into the separation chamber;
 a first outlet port operatively connected to the separation chamber at an upper outlet location, the upper outlet location being above the inlet location during operation;
 a first sensor configured and operatively connected to make first measurements of phase content of fluid adjacent the first outlet port;
 a second outlet port operatively connected to the separation chamber at a lower outlet location, the lower outlet location being below the inlet location during operation;
 a second sensor configured and operatively connected to make second measurements indicative of phase content of fluid adjacent the second outlet port; and
 a pumping system to flow fluid into and out of the separation chamber, the pumping system including a piston and a cylinder, when the pumping system is in use, the cylinder is oriented about an axis tilted from a horizontal plane to enable a degree of pre-separation of the multiphase fluid to occur within the cylinder.

2. A system according to claim 1 wherein the upper outlet location is at or near an uppermost location of the separation chamber and the lower outlet location is at or near a lowermost location of the separation chamber.

3. A system according to claim 1 wherein the separation chamber is elongated about a longitudinal axis, the longitudinal axis being tilted above a horizontal plane.

4. A system according to claim 3 wherein the longitudinal axis is tilted by at least 30 degrees above the horizontal plane.

5. A system according to claim 1 further comprising a third sensor configured and operatively connected to make measurements indicative of phase content of fluid adjacent the inlet port.

6. A system according to claim 1 wherein the cylinder is a first cylinder and the piston is a first reciprocating piston, the pumping system includes the first reciprocating piston within the first cylinder and a second reciprocating piston within a second cylinder.

7. A system according to claim 6 wherein the first and second cylinders are oriented about the axis tilted from the horizontal plane such that a degree of pre-separation of the phase can occur within the cylinders and wherein a fluid leak occurring between the pistons and cylinders is detectable based at least in part on a pressure sensor or phase detector operatively connected to the pumping system.

8. A system according to claim 6 wherein a fluid leak occurring between the pistons and cylinders can be detected based at least in part on a pressure sensor or phase detector operatively connected to the pumping system.

9. A system according to claim 1, wherein the pumping system is operatively connected such that the pumping system can transfer a sample into a sampling bottle, wherein the sampling bottle comprises a piston, and a pressure behind the piston enables the sample to be taken at or very near a pressure of the multiphase fluid.

10. The system according to claim 1, further comprising a controller to process the first measurements and the second measurements and cause the outlet ports to open and close based on the processing to enable the separation chamber to substantially contain, at separate selective times, any one of the gas, oil, and water.

11. The system according to claim 10, wherein the controller is to:
1) enable the separation chamber to substantially contain the gas by causing the discharge of oil and water from the second outlet port and causing the second outlet port to close when the second measurements are associated with the gas;
2) enable the separation chamber to substantially contain the oil by causing the discharge of gas from the first outlet port and causing the first outlet port to close when the first measurements are associated with the oil and causing the discharge of the water from the second outlet port and causing the second outlet port to close when the second measurements are associated with the oil; and
3) enable the separation chamber to substantially contain the water by causing the discharge of the gas and the oil from the first outlet port and causing the first outlet port to close when the first measurements are associated with the water.

12. A method for separating fluid from a multiphase fluid flow, the method comprising:
pumping a multiphase fluid through an inlet port into a separation chamber at an inlet location, the multiphase fluid including gas, oil, and water; and
enabling fluid to exit the separation chamber at either (1) a first outlet port operatively connected to the separation chamber at an upper outlet location, the upper outlet location being above the inlet location, or (2) a second outlet port operatively connected to the separation chamber at a lower outlet location, the lower outlet location being below the inlet location, wherein the pumping includes flowing the multiphase fluid into and out of the separation chamber using a pumping system that includes a piston disposed within a cylinder, the cylinder being oriented about an axis tilted from a horizontal plane to enable a degree of pre-separation of the multiphase fluid to occur within the cylinder.

13. A method according to claim 12, wherein to enable the separation chamber to substantially contain gas, the method further comprises:
enabling fluid to exit the separation chamber at the second outlet port;
sensing the onset of gas exiting the second outlet port indicating the separation chamber is at least nearly full of the gas; and
flowing the gas from the separation chamber into a sample bottle by closing the second outlet port, opening the first outlet port, and directing the gas to the sample bottle.

14. A method according to claim 12 wherein to enable the separation chamber to substantially contain water, the method further comprises:
enabling fluid to exit the separation chamber at the first outlet port;
sensing the onset of water exiting the first outlet port indicating the separation chamber is at least nearly full of the water; and
flowing the water from the separation chamber into a sample bottle by closing the first outlet port, opening the second outlet port, and directing the water to the sample bottle.

15. A method according to claim 12 wherein to enable the separation chamber to substantially contain oil, the method further comprises:
enabling fluid to exit the separation chamber at the first outlet port;
sensing the onset of liquid exiting the first outlet port indicating the separation chamber is at least nearly full of liquid, the liquid including at least one of oil and water;
enabling the multiphase fluid to exit the separation chamber at the second outlet port instead of the first outlet port until sensing of an onset of oil exiting the second outlet port;
enabling fluid to exit the separation chamber at the first outlet port instead of the second outlet port until sensing of the liquid exiting the first outlet port; and
flowing the oil from the separation chamber into a sample bottle.

16. A method according to claim 12, further comprising selectively opening and closing the outlet ports to cause the separation chamber to substantially contain, at separate selective times, any one of the gas, oil, and water.

17. A system for separating fluid from a multiphase fluid including a gas phase, a first liquid phase, and a second liquid phase, the system comprising:
a separation chamber;
an inlet port operatively connected to the separation chamber at an inlet location for flowing each phase of the multiphase fluid into the separation chamber;
an upper outlet port operatively connected to the separation chamber at an upper outlet location, the upper outlet location being above the inlet location during operation;
a first sensor configured and operatively connected to make measurements indicative of phase content of fluid passing through the upper outlet port;
a lower outlet port operatively connected to the separation chamber at a lower outlet location, the lower outlet location being below the inlet location during operation;
a second sensor configured and operatively connected to make measurements indicative of phase content of fluid passing through the lower outlet port; and a pumping system to flow fluid into and out of the separation chamber, the pumping system includes a piston within a cylinder, when the pumping system is in use, the cylinder is oriented about an axis tilted from a horizontal plane to enable a degree of pre-separation of the multiphase fluid to occur within the cylinder.

18. A system according to claim 17 wherein each of the first and second liquid phases is other than oil and water, and one or more chemicals are mixed with the flow to facilitate the separation of the phases.

19. A system according to claim 17 further including a plurality of sensors configured and positioned to detect one or more phases inside the separation chamber.

20. A system according to claim 17 wherein the separation chamber includes a window for visually monitoring of phases present in the separation chamber, the monitoring is performed using a video camera or an indirect measurement light EMR transmittance.

21. A system according to claim 17 wherein the circulation of fluid through the separation chamber is generated using differential pressure between a first multiphase flow port and a second multiphase flow port.

22. A system according to claim 17, further comprising a controller to selectively cause fluid flow out of the outlet ports to enable the separation chamber to contain, at separate selective times, any one of the gas phase, the first liquid phase, and the second liquid phase.

* * * * *